US012702713B2

(12) United States Patent
Armendáriz Borunda et al.

(10) Patent No.: US 12,702,713 B2
(45) Date of Patent: Aug. 11, 2026

(54) SEMI-SOLID, OIL-BASED PHARMACEUTICAL COMPOSITIONS CONTAINING PIRFENIDONE FOR APPLICATION IN TISSUE REPAIR

(71) Applicant: Excalibur Pharmaceuticals, Inc., New York, NY (US)

(72) Inventors: Juan Armendáriz Borunda, Mexico City (MX); José Agustín Rogelio Magaña Castro, Mexico City (MX); Laura Vázquez Cervantes, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 1168 days.

(21) Appl. No.: 17/272,144

(22) PCT Filed: Aug. 23, 2019

(86) PCT No.: PCT/MX2019/000093
§ 371 (c)(1),
(2) Date: Sep. 13, 2021

(87) PCT Pub. No.: WO2020/046102
PCT Pub. Date: Mar. 5, 2020

(65) Prior Publication Data

US 2021/0401989 A1 Dec. 30, 2021

(30) Foreign Application Priority Data

Aug. 31, 2018 (MX) .................. MX/A/2018/010528

(51) Int. Cl.

| | |
|---|---|
| ***A61K 47/10*** | (2017.01) |
| ***A61K 8/49*** | (2006.01) |
| ***A61K 9/00*** | (2006.01) |
| ***A61K 9/06*** | (2006.01) |
| ***A61K 31/4418*** | (2006.01) |
| ***A61K 47/18*** | (2017.01) |
| ***A61K 47/26*** | (2006.01) |
| ***A61K 47/32*** | (2006.01) |
| ***A61Q 19/08*** | (2006.01) |

(52) U.S. Cl.
CPC ............ *A61K 47/10* (2013.01); *A61K 8/4973* (2013.01); *A61K 9/0014* (2013.01); *A61K 9/06* (2013.01); *A61K 31/4418* (2013.01); *A61K 47/18* (2013.01); *A61K 47/26* (2013.01); *A61K 47/32* (2013.01); *A61Q 19/08* (2013.01)

(58) Field of Classification Search
CPC ........................................................ A61K 9/06
See application file for complete search history.

(56) References Cited

U.S. PATENT DOCUMENTS

| | | | |
|---|---|---|---|
| 4,105,782 | A | 8/1978 | Yu et al. |
| 4,256,877 | A | 3/1981 | Karlsson et al. |
| 4,376,118 | A | 3/1983 | Daher et al. |
| 5,009,895 | A | 4/1991 | Lui |
| 5,310,562 | A | 5/1994 | Margolin |
| 5,811,130 | A | 9/1998 | Boettner et al. |
| 5,958,420 | A | 9/1999 | Jenson |
| 6,365,131 | B1 | 4/2002 | Doshi et al. |
| 7,109,246 | B1 | 9/2006 | Hawtin |
| 7,816,383 | B1 | 10/2010 | Bradford et al. |
| 8,492,412 | B2 * | 7/2013 | Magana Castro ..... A61K 47/22 514/354 |
| 8,603,965 | B2 | 12/2013 | Zhou et al. |
| 9,408,836 | B2 | 8/2016 | Armendariz Borunda et al. |
| 9,949,959 | B2 | 4/2018 | Armendariz Borunda et al. |
| 9,962,374 | B2 | 5/2018 | Armendariz Borunda et al. |
| 10,376,500 | B2 | 8/2019 | Magana Castro et al. |
| 10,383,862 | B2 | 8/2019 | Armendariz Borunda et al. |
| 10,792,258 | B2 | 10/2020 | Magana Castro et al. |
| 11,013,727 | B2 | 5/2021 | Armendariz Borunda et al. |
| 11,040,030 | B2 | 6/2021 | Armendariz Borunda et al. |
| 11,052,074 | B2 | 7/2021 | Armendariz Borunda et al. |
| 11,083,719 | B2 | 8/2021 | Magana Castro et al. |
| 11,576,905 | B2 | 2/2023 | Magaña Castro et al. |
| 11,766,426 | B2 | 9/2023 | Armendáriz Borunda et al. |
| 11,779,574 | B2 | 10/2023 | Magaña Castro et al. |
| 12,083,085 | B2 | 9/2024 | Magaña Castro et al. |
| 12,083,106 | B2 | 9/2024 | Armendáriz Borunda et al. |

(Continued)

FOREIGN PATENT DOCUMENTS

| | | | |
|---|---|---|---|
| CA | 2764043 | A1 | 12/2010 |
| CN | 1701793 | A | 11/2005 |

(Continued)

OTHER PUBLICATIONS

International Preliminary Report on Patentability dated Jan. 28, 2018 for Application No. PCT/MX2017/000129.
International Search Report and Written Opinion dated Apr. 9, 2018 for Application No. PCT/MX2017/000129.
International Search Report and Written Opinion, PCT/MX2018/000071, dated Mar. 28, 2019, 12 pages.
International Preliminary Report on Patentability, PCT/MX2018/000071, dated Jul. 19, 2019, 7 pages.
International Preliminary Report on Patentability dated Aug. 7, 2013 for Application No. PCT/MX2012/000067.
International Search Report and Written Opinion dated Nov. 22, 2012 for Application No. PCT/MX2012/000067.

(Continued)

*Primary Examiner* — Bethany P Barham
*Assistant Examiner* — Paul Hoerner
(74) *Attorney, Agent, or Firm* — Wolf, Greenfield & Sacks, P.C.

(57) ABSTRACT

The present invention describes semi-solid pharmaceutical compositions containing Pirfenidone, which offer advantages over other cutaneously administered pharmaceutical forms known in the prior art, due to its permeability and absorption characteristics, which are useful in the treatment for restoring tissues that have suffered loss or degradation of extracellular matrix resulting in the formation of wrinkles or skin thinning.

7 Claims, No Drawings

(56) References Cited

U.S. PATENT DOCUMENTS

2003/0103941 A1 6/2003 Crombleholme et al.
2003/0185872 A1 10/2003 Kochinke et al.
2004/0029946 A1 2/2004 Arora et al.
2004/0235946 A1 11/2004 Ott
2005/0059626 A1 3/2005 Van Nest et al.
2005/0267018 A1 12/2005 Blatt et al.
2006/0039931 A1* 2/2006 Scheiwe ............ A61K 31/4418 514/345
2006/0051339 A1 3/2006 Sivak
2006/0115503 A1 6/2006 Goyal
2006/0198823 A1 9/2006 Blatt
2007/0054842 A1 3/2007 Blatt et al.
2007/0117841 A1 5/2007 Ozes et al.
2007/0128258 A1 6/2007 Faure et al.
2007/0258946 A1 11/2007 Blatt
2008/0025986 A1 1/2008 Ozes et al.
2008/0319026 A1 12/2008 Gant et al.
2009/0047246 A1 2/2009 Beigelman et al.
2009/0137354 A1 5/2009 Chaudhuri
2010/0221217 A1 9/2010 Porter et al.
2010/0256031 A1 10/2010 Wu et al.
2011/0034495 A1 2/2011 Seiwert et al.
2011/0224265 A1 9/2011 Magana Castro et al.
2011/0288134 A1 11/2011 Maksumova et al.
2012/0192861 A1 8/2012 Surber et al.
2012/0283328 A1 11/2012 Modi
2013/0225639 A1 8/2013 Robinson et al.
2013/0245073 A1 9/2013 Magana Castro et al.
2013/0345165 A1 12/2013 Smith et al.
2014/0296300 A1 10/2014 Armendariz Borunda et al.
2015/0148382 A1* 5/2015 Armendariz Borunda .................. A61K 9/0014 514/345
2015/0196543 A1 7/2015 Surber
2015/0231098 A1 8/2015 Magana Castro et al.
2016/0228424 A1 8/2016 Armendariz Borunda et al.
2016/0287567 A1 10/2016 Armendariz Borunda et al.
2016/0338973 A1* 11/2016 Sonti ....................... A61P 31/10
2016/0338997 A1* 11/2016 Ryan ....................... A61P 17/02
2017/0216197 A1* 8/2017 McHale .................. A61P 17/00
2017/0216268 A1 8/2017 Magana Castro et al.
2017/0231937 A1 8/2017 Bolsoy
2018/0066228 A1 3/2018 Smith et al.
2018/0092893 A1 4/2018 Armendariz Borunda et al.
2018/0214434 A1 8/2018 Armendariz Borunda et al.
2018/0353448 A1 12/2018 Magana Castro et al.
2019/0030012 A1 1/2019 Surber
2019/0160048 A1 5/2019 Biber et al.
2019/0262325 A1 8/2019 Armendariz Borunda et al.
2019/0290606 A1 9/2019 Magana Castro et al.
2019/0358213 A1 11/2019 Armendariz Borunda et al.
2020/0016138 A1 1/2020 Magana Castro et al.
2020/0038386 A1 2/2020 Armendariz Borunda et al.
2020/0061040 A1 2/2020 Armendariz Borunda et al.
2020/0253944 A1 8/2020 Magana Castro et al.
2021/0093593 A1 4/2021 Magana Castro et al.
2021/0346360 A1 11/2021 Armendariz Borunda et al.
2021/0386724 A1 12/2021 Armendariz Borunda et al.
2022/0016096 A1 1/2022 Magana Castro et al.
2023/0117397 A1 4/2023 Aguilar-Cordova et al.
2023/0165819 A1 6/2023 Magaña Castro et al.
2023/0181550 A1 6/2023 Armendáriz Borunda et al.
2024/0216350 A1 7/2024 Armendáriz Borunda et al.
2024/0238262 A1 7/2024 Magaña Castro et al.
2025/0213539 A1 7/2025 Armendariz Borunda et al.
2025/0221949 A1 7/2025 Magana Castro et al.
2025/0325530 A1 10/2025 Armendariz Borunda et al.

FOREIGN PATENT DOCUMENTS

CN 101972225 A 2/2011
CN 101972236 A 2/2011
CN 102488660 A 6/2012
CN 102670600 A 9/2012
CN 102670632 A 9/2012
CN 103550242 A 2/2014
EP 1113798 A1 7/2001
EP 1356816 A1 10/2003
EP 2177220 A1 4/2010
EP 2832354 A1 2/2015
EP 2907506 A1 8/2015
ES 2377932 T3 4/2012
ES 2530049 T3 2/2015
JP 8-510251 A 10/1996
JP 2002-506820 A 3/2002
JP 2006-503026 A 1/2006
JP 2011-506446 A 3/2011
JP 2014-505733 A 3/2014
JP 2014-522861 A 9/2014
JP 2015-513359 A 5/2015
JP 2015-526528 A 9/2015
JP 2016-515525 A 5/2016
JP 2016-517444 A 6/2016
KR 10-2014-0057248 A 5/2014
KR 10-2014-0146 A 12/2014
KR 10-2017-0074497 A 6/2017
MX 2013008151 A 10/2013
WO WO 97/10712 A1 3/1997
WO WO 1999/047140 A1 9/1999
WO WO 2000/016775 A1 3/2000
WO WO 2004/073713 A1 9/2004
WO WO 2004/078193 A1 9/2004
WO WO 2004/078194 A1 9/2004
WO WO 2004/078207 A1 9/2004
WO WO 2004/089283 A2 10/2004
WO WO 2005/000227 A2 1/2005
WO WO 2005/013917 A2 2/2005
WO WO 2005/037214 A2 4/2005
WO WO 2006/122154 A2 11/2006
WO WO 2007/038315 A2 4/2007
WO WO 2008/107873 A1 9/2008
WO WO 2009/022899 A1 2/2009
WO WO 2010/054294 A1 5/2010
WO WO 2010/132864 A1 11/2010
WO WO 2012/106382 A1 8/2012
WO WO 2013/012307 A1 1/2013
WO WO 2013/181691 A1 12/2013
WO WO 2014/036487 A1 3/2014
WO WO 2014/055548 A1 4/2014
WO WO 2016/185182 A1 11/2016
WO WO 2017/104725 A1 6/2017
WO WO 2018/088886 A1 5/2018
WO WO 2018/189012 A1 10/2018
WO WO 2019/035705 A2 2/2019
WO WO 2020/227331 A1 11/2020

OTHER PUBLICATIONS

International Preliminary Report on Patentability dated Dec. 1, 2009 for Application No. PCT/MX2008/000107.
International Search Report dated Dec. 9, 2008 for Application No. PCT/MX2008/000107.
International Search Report and Written Opinion dated Jun. 5, 2013 for Application No. PCT/MX2013/000027.
International Preliminary Report on Patentability dated Dec. 19, 2014 for Application No. PCT/MX2013/000099.
International Search Report and Written Opinion dated Aug. 8, 2014 for Application No. PCT/MX2013/000099.
International Search Report and Written Opinion, for Application No. PCT/MX2019/000093, dated Aug. 4, 2020.
International Preliminary Report on Patentability, for Application No. PCT/MX2019/000093, dated Jan. 12, 2021.
[No Author Listed] Understanding Acne Treatment. Retrieved from https:/lwww.Webmd.com/skin-problems-and-treatnnents/acne/understanding-acne-treatnnent#5 on Feb. 4, 2019. 5 pages.
[No Author Listed] allicinnow, “allicin,” retrieved online at: http://www.allicinnow.com/allicin/acne-treatmentl, 2 pages (2010).
Armendariz-Borunda et al., A Controlled Clinical Trial With Pirfenidone in the Treatment of Pathological Skin Scarring Caused by Bums in Pediatric Patients,Annals of Plastic Surgery, vol. 68(1):22-28 (2012).

(56) References Cited

OTHER PUBLICATIONS

Database WPI Section Ch, Week 200629 Thomson Scientific, London, GB; Class B03, AN 2006-273778, WU, Use of pirfenidone for treating hepatic injury and necrosis and acute lung injury. Shanghai Genomics) p. 7; (2005).
Database WPI Section Ch, Week 201139 Thomson Scientific, London, GB; Class A96, AN 2011-D92901, Li X: Sustained-release tablet comprises pirfenidone, substance capable of releasing active ingredient, and additive. Med Pharm Sci& Technology Co , 1 page (2011).
Database WPI Section Ch, Week 201427 Thomson Scientific, London, GB; Class A96, AN 2014-F77081, Deng C et al., Pharmaceutical composition used for treating hepatic fibrosis, liver fibrosis, liver cirrhosis, and liver cancer comprises pirfenidone, inosine, and auxiliary materials. Sichuan Guokang Pharm Co Ltd, 1 page (2014).
Garcia et al., Pirfenidone effectively reverses experimental liver fibrosis. J Hepatol. Dec. 2002;37(6):797-805.
Josling, Peter Josling's PowerPoint on AllicinCenter Products and Their Uses, retrieved from the internet at: http://allicincenter.com/reference.php?id=products, 15 pages (2013).
Macias-Barragan et al., Methyl-1-Phenyl-2- (1H)-Pyridone Treatment Improves Markers of Hepatic Function and Fibrosis in Steatosis Included By High Fat/Carbohydrate Diet. J Hepatology, Abstract of the International Liver Congress™ 2014—49th Annual Meeting of the European Association for the Study of the Liver, Abstract P428:60(1)Suppl.1: S210 (2014).
Macias-Barragan et al., Pirfenidone LP activates PPARalpha and LXRalpha and results in decreased expression of proinflammatory cytokines and improvement of NASH features induced by high fat/carbohydrate diet. Hepatology—Special Issue: The 67th Annual Meeting of the American Association for the Study of Liver Diseases: The Liver Meeting 2016, Abstract No. 1541: vol. 64(SI): 767A-768A: 2 pages (2016).
Nakanishi et al., Pirfenidone inhibits the induction of iNOS stimulated by interleukin-lbeta at a step of NF-kappaE DNA binding in hepatocytes. J Hepatology, vol. 41(5):730-736 (2004).
Ojeda-Duran et al., Evaluation of Safety of a Newly Formulated Pirfenidone in Chronic Kidney Disease: A Non-Randomized Pilot Study in Mexican Patients. J Renal Hepatic Disorders. 2020;4(1):22-30.
Ozes et al., Preclinical activity of pirfenidone (5-methyl -lphenyl -2 (IH) -pyri done) in cell-based models of nonalcoholic steatohepatitis. Hepatology, Abstract 697, 2003;34(4): 495A.
Park et al., Pirfenidone suppressed the development of glomerulosclerosis in the FGS/Kist mouse. J Korean Med Sci. Aug. 2003;18(4):527-33.
Tiwari et al., Applications of Complementary Polymers in HPMC Hydrophilic Extended Release Matrices. Drug Delivery Technology, Formulating Hydrophilic Matrix Systems, 2009;9(7), 7 pages.
Veras-Castillo et al., Controlled clinical trial with pirfenidone in the treatment of breast capsular contracture:Association ofTGF polymorphisms. Annals Plastic Surgery. 2014;70(1):16-22.
International Search Report and Written Opinion, for Application No. PCT/US2021/027335, dated Jul. 12, 2021.
Wang et al., Remdesivir and chloroquine effectively inhibit the recently emerged novel coronavirus (2019-nCOV) in vitro. Cell Res. Mar. 2020;30(3):269-271. doi: 10.1038/s41422-020-0282-0. Epub Feb. 4, 2020. PMID: 32020029; PMCID: PMC7054408.
International Preliminary Report on Patentability dated Oct. 9, 2014 for Application No. PCT/MX2013/000027.
Partial Supplementary European Search Report, dated Apr. 16, 2024 for EP Application No. 21788910.4.
Extended European Search Report, dated Jul. 12, 2024 for EP Application No. 21788910.4.
International Preliminary Report on Patentability, dated Oct. 27, 2022 for Application No. PCT/US2021/027335.
[No Author Listed], Application of addition polymers in hydrophilic hydroxypropyl methylcellulose extended release matrix tablets. Colorcon China, Inc. China Academic Journal Electronic Publishing House. 2022. 3 pages.
[No Author Listed], Efficacy of Pirfenidone Plus MODD in diabetic foot ulcers. NCT02632877. Last updated: Dec. 17, 2015. Retrieved May 17, 2022 from <https://clinicaltrials.gov/ct2/show/NCT02632877?term=NCT02632877>. 8 pages.
[No Author Listed], History of Changes for Study: NCT04282902; A Study to Evaluate the Efficacy and Safety of Pirfenidone With Novel Coronavirus Infection. Feb. 21, 2020. Accessed from <https://classic.clinicaltrials.gov/ct2/history/NCT04282902?V_1=View#StudyPageTop>. 10 pages.
[No Author Listed], Mexico's coronavirus death toll is likely 60% higher than confirmed numbers. Reuters. Mar. 29, 2021. Accessed from <https://www.nbcnews.com/news/latino/mexicos-coronavirus-death-toll-likely-60-higher-confirmed-numbers-rcna531> on Jan. 10, 2023. 3 pages.
[No Author Listed], Severe Outcomes Among Patients with Coronavirus Disease 2019 (COVID-19)—United States, Feb. 12-Mar. 16, 2020. CDC COVID-19 Response Team. MMWR Morb Mortal Wkly Rep. Mar. 27, 2020;69(12):343-346. doi: 10.15585/mmwr.mm6912e2.
Armendáriz-Borunda et al., A pilot study in patients with established advanced liver fibrosis using pirfenidone. Gut. Nov. 2006;55(11):1663-5. doi: 10.1136/gut.2006.107136.
Azuma et al., Double-blind, placebo-controlled trial of pirfenidone in patients with idiopathic pulmonary fibrosis. Am J Respir Crit Care Med. May 1, 2005;171(9):1040-7. doi: 10.1164/rccm.200404-571OC. Epub Jan. 21, 2005.
Bednarek et al., Skin Antiseptics. In:StatPearls. Jan. 2022. Retrieved from https://www.ncbi.nlm.nih.gov/books/NBK507853 Jun. 9, 2022.
Bhatraju et al., Covid-19 in Critically Ill Patients in the Seattle Region—Case Series. N Engl J Med. May 21, 2020;382(21):2012-2022. doi: 10.1056/NEJMoa2004500. Epub Mar. 30, 2020.
Bruss et al., Pharmacokinetics of orally administered pirfenidone in male and female beagles. J Vet Pharmacol Ther. Oct. 2004;27(5):361-7. doi: 10.1111/j.1365-2885.2004.00612.x.
Cain et al., Inhibition of tumor necrosis factor and subsequent endotoxin shock by pirfenidone. Int J Immunopharmacol. Dec. 1998;20(12):685-95. doi: 10.1016/s0192-0561(98)00042-3.
Chen et al., Early detection of nonalcoholic steatohepatitis in patients with nonalcoholic fatty liver disease by using MR elastography. Radiology. Jun. 2011;259(3):749-56. doi: 10.1148/radiol.11101942. Epub Apr. 1, 2011.
Choudhuri et al., SARS-CoV-2 PCR cycle threshold at hospital admission associated with patient mortality. PLoS One. Dec. 31, 2020;15(12):e0244777. doi: 10.1371/journal.pone.0244777.
Didiasova et al., Pirfenidone exerts antifibrotic effects through inhibition of GLI transcription factors. FASEB J. May 2017;31(5):1916-1928. doi: 10.1096/fj.201600892RR. Epub Feb. 1, 2017.
Estes et al., Antifibrotic therapy in simian immunodeficiency virus infection preserves CD4+ T-cell populations and improves immune reconstitution with antiretroviral therapy. J Infect Dis. Mar. 1, 2015;211(5):744-54. doi: 10.1093/infdis/jiu519. Epub Sep. 22, 2014.
Flores-Contreras et al., Treatment with pirfenidone for two years decreases fibrosis, cytokine levels and enhances CB2 gene expression in patients with chronic hepatitis C. Bmc Gastroenterol. Jul. 27, 2014;14:131. doi: 10.1186/1471-230X-14-131.
Gancedo et al., Pirfenidone prevents capsular contracture after mammary implantation. Aesthetic Plast Surg. Jan. 2008;32(1):32-40. doi: 10.1007/s00266-007-9051-4.
Gao et al., Pirfenidone Alleviates Choroidal Neovascular Fibrosis through TGF-β/Smad Signaling Pathway. J Ophthalmol. Feb. 10, 2021;2021:8846708. doi: 10.1155/2021/8846708.
Gennaro, Remington's Pharmaceutical Sciences. 1990; 18th Ed. pp. 1288-1289, 1291-1292.
Gu et al., Pirfenidone inhibits cryoablation induced local macrophage infiltration along with its associated TGFb1 expression and serum cytokine level in a mouse model. Cryobiology. Jun. 2018;82:106-111. doi: 10.1016/j.cryobiol.2018.03.012. Epub Apr. 3, 2018.

(56) References Cited

OTHER PUBLICATIONS

Guo et al., Pirfenidone inhibits epithelial-mesenchymal transition and pulmonary fibrosis in the rat silicosis model. Toxicol Lett. Jan. 2019;300:59-66. doi: 10.1016/j.toxlet.2018.10.019. Epub Oct. 28, 2018.
Güvenç et al., Pirfenidone Attenue Epidural Fibrosis In Rats By Suppressing TNF-α, IL-1, and α-SMA. J Turk Spin Surg. Jul. 2018;29(3):133-40.
Horie et al., Emerging pharmacological therapies for ARDS: COVID-19 and beyond. Intensive Care Med. Dec. 2020;46(12):2265-2283. doi: 10.1007/s00134-020-06141-z. Epub Jul. 11, 2020.
Huang et al., Clinical features of patients infected with 2019 novel coronavirus in Wuhan, China. Lancet. Feb. 15, 2020;395(10223):497-506. doi: 10.1016/S0140-6736(20)30183-5. Epub Jan. 24, 2020. Erratum in: Lancet. Jan. 30, 2020.
Ishinaga et al., TGF-β induces p65 acetylation to enhance bacteria-induced NF-κB activation. EMBO J. Feb. 21, 2007;26(4):1150-62. doi: 10.1038/sj.emboj.7601546. Epub Feb. 1, 2007.
Janka-Zires et al., Topical Administration of Pirfenidone Increases Healing of Chronic Diabetic Foot Ulcers: A Randomized Crossover Study. J Diabetes Res. 2016;2016:7340641. doi: 10.1155/2016/7340641. Epub Jul. 10, 2016.
King et al., A phase 3 trial of pirfenidone in patients with idiopathic pulmonary fibrosis. N Engl J Med. May 29, 2014;370(22):2083-92. doi: 10.1056/NEJMoa1402582. Epub May 18, 2014. Erratum in: N Engl J Med. Sep. 18, 2014;371(12):1172.
Loomba et al., GS-0976 Reduces Hepatic Steatosis and Fibrosis Markers in Patients With Nonalcoholic Fatty Liver Disease. Gastroenterology. Nov. 2018;155(5):1463-1473.e6. doi: 10.1053/j.gastro.2018.07.027. Epub Jul. 27, 2018.
Lopez-De La Mora et al., Role and New Insights of Pirfenidone in Fibrotic Diseases. Int J Med Sci. Oct. 14, 2015;12(11):840-7. doi: 10.7150/ijms.11579.
Mccommis et al., Treating Hepatic Steatosis and Fibrosis by Modulating Mitochondrial Pyruvate Metabolism. Cell Mol Gastroenterol Hepatol. 2019;7(2):275-284. doi: 10.1016/j.jcmgh.2018.09.017. Epub Oct. 10, 2018.
Moises et al., A Double-blind, Multicenter Study Comparing Pirfenidone and Prednisone for Moderate-to-Severe Pulmonary Fibrosis. Chest J. Jan. 1, 2003;124(4)Suppl:116S. Abstract Only. doi: 10.1378/chest.124.4_MeetingAbstracts.116S-b.
Nagai et al., Open-label compassionate use one year-treatment with pirfenidone to patients with chronic pulmonary fibrosis. Intern Med. Dec. 2002;41(12):1118-23. doi: 10.2169/internalmedicine.41.1118.
Nakazato et al., A novel anti-fibrotic agent pirfenidone suppresses tumor necrosis factor-alpha at the translational level. Eur J Pharmacol. Jun. 20, 2002;446(1-3):177-85. doi: 10.1016/s0014-2999(02)01758-2.
Oku et al., Pirfenidone suppresses tumor necrosis factor-alpha, enhances interleukin-10 and protects mice from endotoxic shock. Eur J Pharmacol. Jun. 20, 2002;446(1-3):167-76. doi: 10.1016/s0014-2999(02)01757-0.
Olivas-Martinez et al., In-hospital mortality from severe COVID-19 in a tertiary care center in Mexico City; causes of death, risk factors and the impact of hospital saturation. PLoS One. Feb. 3, 2021;16(2):e0245772. doi: 10.1371/journal.pone.0245772. Erratum in: PLoS One. May 23, 2022;17(5):e0269053.
Orozco et al., Economic evaluation of topical administration of gel with pirfenidone (KITOSCELL Q®) as an adjuvant in the treatment of patients with diabetic foot ulcers. PMD63. Value in Health. May 2017; 20(5):A246.
Pepin, K., Liver Fat Does Not Affect Liver Stiffness Measured with MR Elastography. Resoundant Fact Sheet. 2019. Accessed from < https://www.resoundant.com/single-post/2019/05/21/fact-sheet-liver-fat-does-not-affect-liver-stiffness-measured-with-mr-elastography> on Sep. 21, 2022. 2 pages.
Raghu et al., Treatment of idiopathic pulmonary fibrosis with a new antifibrotic agent, pirfenidone: results of a prospective, open-label Phase II study. Am J Respir Crit Care Med. Apr. 1999;159(4 Pt 1):1061-9. doi: 10.1164/ajrccm.159.4.9805017.
Rao et al., A Systematic Review of the Clinical Utility of Cycle Threshold Values in the Context of COVID-19. Infect Dis Ther. Sep. 2020;9(3):573-586. doi: 10.1007/s40121-020-00324-3. Epub Jul. 28, 2020. Erratum in: Infect Dis Ther. Aug. 18, 2020.
Ravishankar et al., A brief review on Pleiotropic effects of Pirfenidone—novel and ongoing outcomes. Int J Res Dev Pharm Life Sci. Jan.-Feb. 2019;8(1):6-14. doi: 10.21276/IJRDPL.2278-0238.2019.8(1).6-14.
Rubino et al., Effect of food and antacids on the pharmacokinetics of pirfenidone in older healthy adults. Pulm Pharmacol Ther. Aug. 2009;22(4):279-85. doi: 10.1016/j.pupt.2009.03.003. Epub Mar. 27, 2009.
Ruwanpura et al., Pirfenidone: Molecular Mechanisms and Potential Clinical Applications in Lung Disease. Am J Respir Cell Mol Biol. Apr. 2020;62(4):413-422. doi: 10.1165/rcmb.2019-0328TR.
Salazar-Montes et al., Potent antioxidant role of pirfenidone in experimental cirrhosis. Eur J Pharmacol. Oct. 24, 2008;595(1-3):69-77. doi: 10.1016/j.ejphar.2008.06.110. Epub Jul. 9, 2008.
Schaefer et al., Antifibrotic activities of pirfenidone in animal models. Eur Respir Rev. Jun. 2011;20(120):85-97. doi: 10.1183/09059180.00001111.
Seifirad, S., Pirfenidone: A novel hypothetical treatment for COVID-19. Med Hypotheses. Nov. 2020;144:110005. doi: 10.1016/j.mehy.2020.110005. Epub Jun. 17, 2020.
Selman et al., Idiopathic pulmonary fibrosis: prevailing and evolving hypotheses about its pathogenesis and implications for therapy. Ann Intern Med. Jan. 16, 2001;134(2):136-51. doi: 10.7326/0003-4819-134-2-200101160-00015.
Selvaraj et al., Diagnostic accuracy of elastography and magnetic resonance imaging in patients with NALFD: A systematic review and meta-analysis. J Hepatol. Oct. 2021;75(4):770-785. doi: 10.1016/j.jhep.2021.04.044. Epub May 13, 2021.
Suga et al., Preventive effect of pirfenidone against experimental sclerosing peritonitis in rats. Exp Toxicol Pathol. Sep. 1995;47(4):287-91. doi: 10.1016/s0940-2993(11)80261-7.
Sun et al., Pharmacokinetic and pharmacometabolomic study of pirfenidone in normal mouse tissues using high mass resolution MALDI-FTICR-mass spectrometry imaging. Histochem Cell Biol. Feb. 2016;145(2):201-11. doi: 10.1007/s00418-015-1382-7. Epub Dec. 8, 2015.
Sun et al., Pharmacometabolic response to pirfenidone in pulmonary fibrosis detected by MALDI-FTICR-MSI. Eur Respir J. Sep. 15, 2018;52(3):1702314. doi: 10.1183/13993003.02314-2017.
Vitiello et al., COVID-19 Patients with Pulmonary Fibrotic Tissue: Clinical Pharmacological Rational of Antifibrotic Therapy. SN Compr Clin Med. 2020;2(10):1709-1712. doi: 10.1007/s42399-020-00487-7. Epub Aug. 27, 2020.
Wang et al., Clinical Features of 69 Cases With Coronavirus Disease 2019 in Wuhan, China. Clin Infect Dis. Jul. 28, 2020;71(15):769-777. doi: 10.1093/cid/ciaa272.
Wilson et al., Another Weapon in the Battle against Idiopathic Pulmonary Fibrosis? Am J Respir Cell Mol Biol. Apr. 2019;60(4):386-387. doi: 10.1165/rcmb.2018-0387ED.
Wu et al., Risk Factors Associated With Acute Respiratory Distress Syndrome and Death in Patients With Coronavirus Disease 2019 Pneumonia in Wuhan, China. JAMA Intern Med. Jul. 1, 2020;180(7):934-943. doi: 10.1001/jamainternmed.2020.0994. Erratum in: JAMA Intern Med. Jul. 1, 2020;180(7):1031.
Wygrecka et al., Pirfenidone exerts anti-fibrotic effects through Inhibition of GLI transcription factors. Pneumologie. Feb. 21, 2018;72(S 01):S114-5. doi: 10.1055/s-0037-1619431.
Zhang et al., Liver fibrosis imaging: A clinical review of ultrasound and magnetic resonance elastography. J Magn Reson Imaging. Jan. 2020;51(1):25-42. doi: 10.1002/jmri.26716. Epub Mar. 12, 2019. Author Manuscript, 32 pages.
Zhang et al., Pirfenidone reduces fibronectin synthesis by cultured human retinal pigment epithelial cells. Aust N Z J Ophthalmol. May 1998;26 Suppl 1:S74-6. doi: 10.1111/j.1442-9071.1998.tb01380.x.
Zhou et al., Clinical course and risk factors for mortality of adult inpatients with COVID-19 in Wuhan, China: a retrospective cohort study. Lancet. Mar. 28, 2020;395(10229):1054-1062. doi: 10.1016/

(56) References Cited

OTHER PUBLICATIONS

S0140-6736(20)30566-3. Epub Mar. 11, 2020. Erratum in: Lancet. Mar. 28, 2020;395(10229):1038. Erratum in: Lancet. Mar. 28, 2020;395(10229):1038.
Ziol et al., Noninvasive assessment of liver fibrosis by measurement of stiffness in patients with chronic hepatitis C. Hepatology. Jan. 2005;41(1):48-54. doi: 10.1002/hep.20506.
No Author Listed, A randomized, open-label study to evaluate the efficacy and safety of Pirfenidone in patients with severe and critical novel coronavirus infection (COVID-19). World Health Organization International Clinical Trials Registry. Feb. 28, 2020. Accessed from <https://trialsearch.who.int/Trial2.aspx?TrialID=ChiCTR2000030333>. 3 pages.
No Author Listed, Efficacy and Safety of Pirfenidone in the Treatment of Severe Post-Novel Coronavirus Pneumonia (COVID-19)) Fibrosis: a prospective exploratory experimental medical study. World Health Organization International Clinical Trials Registry. Mar. 6, 2020. Accessed from <https://trialsearch.who.int/Trial2.aspx?TrialID=ChiCTR2000030892>. 2 pages.
Dai et al., High-resolution Chest CT Features and Clinical Characteristics of Patients Infected with COVID-19 in Jiangsu, China. Int J Infect Dis. Jun. 2020;95:106-112. doi: 10.1016/j.ijid.2020.04.003. Epub Apr. 6, 2020.
Lewis, T., Here's what we know about the most touted drugs tested for COVID-19. Scientific American. Apr. 16, 2020. Accessed May 16, 2025 from <https://www.scientificamerican.com/article/heres-what-we-know-about-the-most-touted-drugs-tested-for-covid-19/>. 10 pages.
Lovelace et al., Dr. Anthony Fauci warns US could 'be in for a bad fall' if coronavirus treatments don't work. CNBC, Health and Science. Apr. 28, 2020. Accessed May 16, 2025 from <https://rb.gy/a2pf8q>. 3 pages.
Xu et al., Key Points of Clinical and CT Imaging Features of 2019 Novel Coronavirus (2019-nCoV) Imported Pneumonia Based On 21 Cases Analysis. medRxiv. Mar. 6, 2020. doi: 10.1101/2020.03.03.20030775. 14 pages.
*U.S. Appl. No. 18/965,593, filed Dec. 2, 2024, Armendáriz Borunda et al.
*U.S. Appl. No. 17/328,685, filed May 24, 2021, Armendáriz Borunda et al.
*U.S. Appl. No. 17/351,151, filed Jun. 17, 2021, Armendáriz Borunda et al.
*U.S. Appl. No. 17/390,368, filed Jul. 30, 2021, Magana Castro et al.
PCT/US2021/027335, Jul. 12, 2021, International Search Report and Written Opinion.

* cited by examiner

SEMI-SOLID, OIL-BASED PHARMACEUTICAL COMPOSITIONS CONTAINING PIRFENIDONE FOR APPLICATION IN TISSUE REPAIR

RELATED APPLICATIONS

This application is a national stage filing under 35 U.S.C. § 371 of International PCT Application No. PCT/MX2019/000093, filed Aug. 23, 2019, which claims priority to Mexican Application, MX/a/2018/010528, filed Aug. 31, 2018, each of which is incorporated herein by reference.

FIELD OF THE INVENTION

The present invention relates to semi-solid formulations in the form of an unguent, gel, cream, or ointment, containing Pirfenidone as an active ingredient, which offer advantages in the treatment and prevention of fibrotic lesions over other cutaneously administered pharmaceutical forms known in the prior art.

BACKGROUND OF THE INVENTION

The present invention relates to semi-solid pharmaceutical compositions and their use in the treatment for repairing fibrotic lesional tissues and for preventing fibrotic lesions, compositions comprising 5-methyl-1-phenyl-2(1H)-pyridone as an active anti-fibrotic ingredient.

Pirfenidone is a non-peptide synthetic molecule with a molecular weight of 185.23 daltons. Its chemical elements are expressed as $C_{12}H_{11}NO$, and its structure is known. The synthesis of pirfenidone has been worked out. Pirfenidone is manufactured and clinically evaluated as a broad-spectrum anti-fibrotic drug. Pirfenidone has anti-fibrotic properties through decreased TNF-$\alpha$ expression, decreased PDGF expression, and decreased collagen expression. 5-Methyl-1-phenyl-2(1H)-pyridone has the following structural formula:

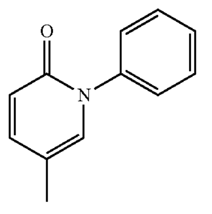

U.S. Pat. Nos. 3,974,281; 4,042,699; and 4,052,509 further disclose the use of the compound 5-methyl-1-phenyl-2-(1H)-pyridone ("pirfenidone") for reducing serum uric acid and glucose levels, for treating inflammatory upper respiratory tract conditions, and for treating inflammatory skin conditions in humans and other mammals.

The use of pirfenidone in the repair and prevention of fibrotic lesions is disclosed in Patents EP-A-0383591 and EP-A-0702551.

Accordingly, it is a main object of the present invention to provide semi-solid compositions for repairing and preventing fibrotic lesional tissue.

Herein, the term "anti-fibro", "anti-fibrotic" or "anti-fibrosis" refers to the repairs and/or prevention of pathological collagen polymerization, collagen disease, wrinkles, etc., and repair as well as normalization of existing pathological fibrotic tissues.

It is a further object of the invention to provide such semi-solid compositions comprising 5-methyl-1-phenyl-2-(1H)-pyridone ("pirfenidone") as an active anti-fibrotic ingredient.

Other objects of the present invention as well as particular features and advantages thereof will be explained in, or will be apparent from the following description.

OBJECT OF THE INVENTION

The present invention describes semi-solid pharmaceutical compositions containing Pirfenidone, which offer advantages over other cutaneously administered pharmaceutical forms known in the prior art, due to its permeability and absorption characteristics, which are useful in the treatment for restoring tissues that have suffered loss or degradation of extracellular matrix resulting in the formation of wrinkles or skin thinning. That is, to show that the use of the semi-solid composition containing Pirfenidone is effective in restoring skin imperfections caused by the loss of collagen and other extracellular matrix proteins such as fibronectin and elastin.

Another object of the present invention is to provide semi-solid compositions in the form of a cream, ointment and unguent for cutaneous administration comprising Pirfenidone as an active ingredient; an absorption base; a solubilizer; a preservative; an emollient agent, and purified water.

DESCRIPTION OF THE INVENTION

5-Methyl-1-phenyl-2(1H)-pyridone, pirfenidone, is the main constituent of the semi-solid composition of the present invention that induces "the filling" of the skin that has undergone the degradation of extracellular matrix proteins such as collagens, fibronectin, and elastin.

Different resources and treatments have been used to the date and none of them have shown to be actually effective. Pirfenidone has shown its efficacy as an anti-fibrotic agent in different pathologies and organs, as demonstrated in previous works, where we have seen an effect on the fibroblasts and the collagen produced by them in both experimental models and clinical tests.

Recently obtained additional information allows us to conclude that Pirfenidone induces the expression of transcription factors involved in the ignition of genes stimulating collagen and non-collagen protein degradation. However, depending on the micro-environment in which Pirfenidone is immersed, in the absence of excess extracellular matrix (such as cases of diabetic foot ulcers and varicose ulcers wherein there is extensive tissue loss and absence of extracellular matrix producing and synthesizing cells, formation of facial wrinkles, and thinning and loss of skin elasticity), it will induce precisely the opposite effect to that previously reported with regard to its ability to induce collagenases (enzymes that degrade collagens) for remodeling scars.

Ointments and Unguents

An unguent is defined as a soft-consistency preparation containing the drug(s) and additives incorporated into an appropriate base that provides it with body and consistency. It adheres and applies to the skin and mucous membranes. The base can be liposoluble or water soluble, it is generally anhydrous or has at the most 20 percent water. When contained a washable or water-removable base, it is also referred to as a hydrophilic unguent, also known as an ointment.

The definition of ointment was introduced in the USP in 1955. The definition is broad and includes petrolatum bases, that is, water-in-oil (W/O) or oil-in-water (O/W) emulsion bases and the so-called water-soluble bases.

They are selected or designed for optimal drug dispersion and also to impart emollient properties or other medicinal feature, since they are designed for specific uses and to facilitate their application.

A base must not be irritating, it must be easy to remove, it must not stain, it must be stable, it must not depend on pH and it must be widely compatible with a variety of drugs.

The technical advantage from the use of formulations in the form of creams or unguents over the prior art in gel formulations consists substantially of the following properties attributable to the type of formulation: Satisfactory antioxidant stability, good physiological tolerability, sufficient release of Pirfenidone, good sensitivity; the objective pursued by the application of the ointment on the skin is that the drug deeply penetrates into the skin unlike the previous formulations, the therapeutic effect of which exhibits efficacy on wounds or skin lesions.

By means of most of the ointments used, a local therapy is attempted.

Before the drug can penetrate the skin, it must be released from the ointment base.

One criterion for the suitability of an ointment base in therapy is the transfer rate of the drug.

By rubbing or massaging, the drug penetration is doubled or tripled.

CERATE: when the ointment contains wax in a ratio of at least 25%.

GLICEROLATE: when it contains at least 50% glycerin.

UNGUENTS: Semi-solid preparations intended for external application on the skin or mucous membranes and which employ fats and/or resins as vehicles.

PASTES: They are semi-solid pharmaceutical forms containing a high percentage of solids and are intended for topical application. They can be prepared from an aqueous gel or from fatty excipients having, in these cases, thick unguents that do not usually soften at body temperature and consequently, serve as protective layers in areas on which they are applied.

CREAMS: They are emulsified semi-solid pharmaceutical forms containing one or several active ingredients and a water content of from 20 to 80%. This term has traditionally been applied to semi-solid materials that have a relatively fluid formulated consistency; either as a water-in-oil or oil-in-water emulsion. However, more recently the term has been restricted to products consisting of oil-in-water emulsions or aqueous microcrystalline dispersions of fatty acids or long chain alcohols that are easily washable, cosmetically and aesthetically more acceptable.

They are pharmaceutical forms made up of two phases, one lipophilic and the other aqueous.

They have a soft consistency and a Newtonian or pseudoplastic flow due to their high water content.

A difference between the cream and the ointment is that the ointment hardly flows and the creams easily flow, also the ointments are always monophasic.

Non-penetrating or epidermal: they are intended for protection against certain physical or chemical agents, lubricants, softeners, astringents, emollients or keratolytic, caustic, keratoplastic, refreshing agents.

Dermal or endodermal: rubefacients, healing, antipruritics.

Subdermal or hypodermal: local anaesthetics, hormones, vitamins, anti-rheumatic agents.

Semi-Solid Composition

The semi-solid composition containing from 2% to 12% Pirfenidone is made by using from 20% to 60% of a solvent-humectant, from 5% to 10% of one or a combination of emulsifiers, from 2% to 8% of a consistency and emollience agent, from 0.5% to 3% of one or various emollients, from 0.1% to 2% of a preservative, from 0.05% to 0.2% of a rheological or viscosity agent, from 0.05% to 0.2% of a neutralizer, from 0.05% to 0.2% of a preservative, and from 0.0005% to 0.003% of a stabilizer, and optionally, from 0.008 to 0.8% of an antiseptic/preservative.

Wherein the solvent-humectant is selected from the group consisting of Glycerin, Ethyl alcohol, Transcutol-P, N-Methylpyrrolidone, 2-pyrrolidone, Cremophor RH-40, Propylene Glycol; the emulsifiers are selected from the group consisting of Cetyl alcohol, Stearyl alcohol, Cetostearyl alcohol, Span 80, Span 60, Glyceryl monostearate, Polyethylene glycol stearate, Cremophor A-6, Cetostearyl alcohol, Cetyl alcohol, Glyceryl monostearate, Spermaceti, Cremophor A-25; the consistency and emollience agents are selected from the group consisting of Cetostearyl alcohol, Macrogol cetostearyl ether, Ceterareth-25, Cetyl alcohol, Spermaceti, Beeswax, Glyceryl monostearate, Solid Paraffin, Cetyl alcohol, and Stearyl alcohol; the emollient is selected from the group consisting of Dimeticon, Mineral oil, Isopropyl adipate, Isohexadecane, Capryl/caprylic triglyceride, Myristyl glucoside, Behenyl alcohol, C12-15 Alkylbenzoate, isopropyl isostearate; the preservative is selected from the group consisting of Sodium Methylparaben, Sodium propylparaben, Phenoxyethanol, Diazolinidyl urea, Iodopropynyl butylcarbamate; the viscosity agent is selected from the group consisting of Sodium propylparaben, the neutralizer may be Triethanolamine or Sodium hydroxide; the stabilizer can be selected from the family of Citric acid or synthetic Vitamin C.

For a better understanding of the invention, the process of preparing the semi-solid composition containing pirfenidone and illustrative examples of the use and application thereof are shown below.

Semi-solid composition prepared according to the following process:

1. Process of manufacturing a semi-solid pirfenidone pharmaceutical composition in the form of a cream, comprising the following steps:

A) Oily Phase

Placing Span 60, Cetyl Alcohol, Stearyl Alcohol, Cremophor A-6, Cremophor A-25 and Dimethicone in a reactor, stirring and heating to (75° C.-80° C.), until completely melted.

Identify Oily Phase

B) Mixture A

Placing 30% of the total purified water in a suitable-capacity, stainless steel container, and gradually adding the carbomer while stirring constantly until completely humidified.

Identify Mixture A

C) Solution "A"

Placing propylene glycol in a pot and heating to (75° C.-80° C.), and stirring at 131 rpm±10%.

Gradually adding Pirfenidone while stirring constantly and maintaining heating to (75° C.-80° C.) until completely dissolved. Maintaining for 30 min.

(Identify Solution "A")

D) Solution "B"

Placing 30% of the total water to be used in a suitable-capacity, stainless steel container;

gradually adding: Sodium Methylparaben, Sodium Propylparaben, Anhydrous Citric Acid, Polysorbate 60 to said container while stirring constantly until completely dissolved.

Identify as Solution "B"

E) Aqueous Phase

Gradually adding the contents of the MIXTURE "A" and SOLUTION "B" to the Solution identified as "A" while stirring constantly and maintaining heating to (75° C.-80° C.). Maintain stirring at 131 rpm±10% and heating until completely incorporated.

Identify as Aqueous Phase

F) Phase Mixture

Adding the AQUEOUS PHASE to the reactor having the OILY PHASE while stirring constantly at a constant temperature of 75° C.-80° C. Maintaining constant stirring at 71 rpm±10%, for 20 minutes and lowering the mixture temperature to 40° C.-45° C.

G) Solution "C"

Separately placing the remaining water in a stainless steel container and gradually adding triethanolamine to said container while stirring constantly until completely dissolved.

Identify Solution "C"

H) Final Mixture

Adding SOLUTION C to the reactor, stirring at 71 rpm±10%, for 60 minutes or until reaching a temperature of 30° C.-35° C.

2. Process of manufacturing a semi-solid pirfenidone pharmaceutical composition in the form of an ointment, comprising the following steps:

A) Oily Phase

Placing: Span 60, Cetyl Alcohol, Stearyl Alcohol, Cremophor A-6, Cremophor A-25 and White Sodium Petrolatum in a reactor, stirring and heating to (75° C.-80° C.), until completely melted.

Identify Oily Phase

B) Solution "A"

Placing Propylene glycol in a pot and heating to 75° C.-80° C. and stirring at 131 rpm±10%, and stirring. Gradually adding Pirfenidone while stirring constantly and maintaining heating to (75° C.-80° C.) until completely dissolved. Maintaining under stirring and heating for 20 minutes, gradually adding M-DDO 2%, stirring for 10 min; adding Tween 60 and stirring for 10 min.

C) Phase Mixture

Adding all the contents of the AQUEOUS PHASE to the reactor having the OILY PHASE, while constantly stirring at 71 rpm for 20 min. Lowering temperature to 30-35° C.

3. Process of manufacturing a semi-solid pirfenidone pharmaceutical composition in the form of an unguent, comprising the following steps:

A) Oily Phase

Placing: Span 60, Stearyl Alcohol, and Sodium White Petrolatum in a reactor, stirring and heating to (75° C.-80° C.), until completely melted.

Identify Oily Phase

B) Solution "A"

Placing Propylene glycol in a pot and heating to 75° C.-80° C. and stirring at 131 rpm±10%, and stirring. Gradually adding Pirfenidone while stirring constantly and maintaining heating to (75° C.-80° C.) until completely dissolved. Maintaining under stirring and heating for 20 minutes, gradually adding M-DDO 2%, stirring for 10 min; adding Tween 60 and stirring for 10 min.

C) Solution "B"

Placing Purified Water in a suitable-capacity, stainless steel container and gradually adding citric acid and polysorbate 60.

D) Aqueous Phase

Gradually adding the solution "B" to the Solution identified as "A", while stirring constantly and maintaining heating to 75° C.-80° C., maintaining for 30 minutes.

E) Aqueous Phase

Adding the AQUEOUS PHASE to the reactor having the OILY PHASE, while stirring constantly at a constant temperature for 20 min.

EXAMPLES

Example of a cream-type semi-solid composition is shown in Table 1:

TABLE 1

Example of a cream-type semi-solid formulation

| INGREDIENT NAME | FUNCTION | AMOUNT (g) |
|---|---|---|
| Pirfenidone | Active ingredient | 10 |
| Propylene glycol | Solvent, Humectant | 50 |
| Span 60 | Emulsifier | 6.382 |
| Cetyl alcohol | Consistency and emollience agent | 2 |
| Stearyl alcohol | Consistency and emollience agent | 2 |
| Cremophor A-6 | Emulsifier | 1 |
| Cremophor A-25 | Emulsifier | 1 |
| Dimethicone | Emollient | 1 |
| Tween 60 | Emulsifier | 0.617 |
| Sodium Methylparaben | Preservative | 0.147 |
| Carbomer | Rheological or viscosity agent | 0.100 |
| Triethanolamine | Neutralizer | 0.100 |
| Sodium Propylparaben | Preservative | 0.066 |
| Anhydrous Citric Acid | Stabilizer | 0.001 |
| Purified Water q.s. | | 100 |

Example of an ointment-type semi-solid composition is shown in Table 2:

TABLE 2

Example of an ointment-type semi-solid composition

| ADDITIVE NAME | FUNCTION | AMOUNT (g) |
|---|---|---|
| Pirfenidone | Active ingredient | 10 |
| Propylene glycol | Solvent, Humectant | 10 |

TABLE 2-continued

| Example of an ointment-type semi-solid composition | | |
|---|---|---|
| ADDITIVE NAME | FUNCTION | AMOUNT (g) |
| Span 60 | Emulsifier | 18.234 |
| Cetyl alcohol | Consistency and emollience agent | 1 |
| Stearyl alcohol | Consistency and emollience agent | 1 |
| Cremophor A-6 | Emulsifier | 1 |
| Cremophor A-25 | Emulsifier | 1 |
| Solid white petrolatum | Consistency base | 100 |
| Tween 60 | Emulsifier | 2.122 |
| M-DDO 2% | Antiseptic/Preservative | 0.8 |

Example of an unguent-type semi-solid composition is shown in Table 3:

TABLE 3

| Example of an unguent-type semi-solid composition | | |
|---|---|---|
| ADDITIVE NAME | FUNCTION | Amount (g) |
| Pirfenidone | Active ingredient | 10.000 |
| Propylene glycol | Solvent, Humectant | 45.000 |
| Span 60 | Emulsifier | 18.234 |
| Tween 60 | Emulsifier | 1.764 |
| Stearyl Alcohol | Consistency and emollience agent | 3.000 |
| Citric acid | Conservative | 0.001 |
| M-DDO 2% | Antiseptic/preservative | 0.800 |
| Solid White Petrolatum | Consistency Base | 17.000 |
| Purified water q.s. | Solvent | 100.000 |

Although the present invention has been described with respect to a limited number of embodiments, the specific features of one embodiment should not be attributed to other embodiments of the invention. A single embodiment is not representative of all aspects of the invention. In some embodiments, the compositions or methods may include several compounds or steps not mentioned herein. In other embodiments, the compositions or methods do not include, or are substantially free of compounds or steps not indicated herein. There are variations and modifications based on the described embodiments.

The invention claimed is:

1. A semi-solid pirfenidone pharmaceutical composition comprising:

(a) from 2% to 12% w/w pirfenidone;
(b) from 20% to 60% w/w of propylene glycol;
(c) from 5% to 10% w/w total of one or more of sorbitan stearate, ceteareth-6 and stearyl alcohol, ceteareth-25, and polysorbate 60;
(d) from 2% to 8% w/w total of one or more of cetyl alcohol and stearyl alcohol;
(e) from 0.5% to 3% w/w of one or more dimethicone;
(f) from 0.1% to 2% w/w of sodium methylparaben;
(g) from 0.05% to 0.2% w/w of carbomer;
(h) from 0.05% to 0.2% w/w of triethanolamine;
(i) from 0.05% to 0.2% w/w of sodium propylparaben; and
(j) from 0.0005% to 0.003% w/w of citric acid;

wherein the semi-solid pharmaceutical composition is in the form of a cream.

2. The semi-solid pirfenidone pharmaceutical composition according to claim 1, wherein the composition comprises:

(a) from 2% to 12% w/w Pirfenidone;
(b) 50% w/w Propylene Glycol;
(c) 6.382% w/w sorbitan stearate;
(d) 2% w/w Cetyl Alcohol;
(e) 2% w/w Stearyl alcohol;
(f) 1% w/w ceteareth-6 and stearyl alcohol;
(g) 1% w/w ceteareth-25;
(h) 1% w/w Dimethicone;
(i) 0.617% w/w polysorbate 60;
(j) 0.147% w/w Sodium Methylparaben;
(k) 0.1% w/w Carbomer;
(l) 0.1% w/w_Triethanolamine;
(m) 0.066% w/w Sodium Propylparaben;
(n) 0.001% w/w Citric acid; and
(o) Water qs 100%.

3. The semi-solid pirfenidone pharmaceutical composition of claim 1 further comprising from 0.008% to 0.8% of an antiseptic/preservative.

4. A method of manufacturing the semi-solid pirfenidone pharmaceutical composition according to claim 1, the method comprising:

(1) Stirring sorbitan stearate, Cetyl Alcohol, Stearyl Alcohol, ceteareth-6 and stearyl alcohol, ceteareth-25, and Dimethicone and heating at 75-80° C.;
(2) Adding carbomer to 30% of the total water in the composition;
(3) Heating propylene glycol to 75-80° C. and stirring, before gradually adding Pirfenidone while stirring constantly and heating at 75-80° C.;
(4) Maintaining stirring and heating of the reaction of step 3 for 30 min;
(5) Gradually adding Sodium Methylparaben, Sodium Propylparaben, Citric Acid, and Tween 60 (Polysorbate 60 to 30% of the total water in the composition while stirring constantly until completely dissolved;
(6) Gradually adding the contents of step 2 and step 5 to the solution of step 4 while stirring constantly and maintaining heating at 75-80° C.;
(7) Adding the mixture of step 6 to the mixture of step 1 while stirring at 75-80° C. and then maintaining stirring for 20 minutes and lowering the mixture temperature to 40-45° C.;
(8) Gradually adding triethanolamine to the remaining 60% of the total water in the composition while stirring constantly until completely dissolved; and
(9) Adding the solution of step 8 to the mixture of step 7 while stirring for 60 minutes or until reaching a temperature of 30-35° C.

5. A method of restoring skin imperfections caused by the loss of collagen and other extracellular matrix proteins, the method comprising administering the semi-solid pirfenidone pharmaceutical composition according to claim 1 to the skin of an individual in need of said treatment.

6. The method of claim 5, wherein the extracellular matrix proteins are fibronectin and elastin.

7. A method of treating wrinkles and/or skin thinning comprising administering the semi-solid pirfenidone pharmaceutical composition of claim 1 to the skin of an individual in need of said treatment.

* * * * *